United States Patent [19]

Magid et al.

[11] 4,334,863
[45] Jun. 15, 1982

[54] ILLUMINATOR FOR DENTAL HANDPIECE

[75] Inventors: Kenneth S. Magid, Somers; William J. Becker, Hauppauge, both of N.Y.

[73] Assignee: Kinetic Instruments Inc., Bethel, Conn.

[21] Appl. No.: 244,364

[22] Filed: Mar. 16, 1981

Related U.S. Application Data

[63] Continuation of Ser. No. 129,511, Mar. 11, 1980, abandoned, and a continuation-in-part of Ser. No. 953,726, Oct. 19, 1978, abandoned.

[51] Int. Cl.$^3$ .............................................. A61C 3/00
[52] U.S. Cl. ................................................ 433/29
[58] Field of Search ............ 433/29; 350/96.20, 96.21; 362/32

[56] References Cited

U.S. PATENT DOCUMENTS

| | | | |
|---|---|---|---|
| 3,897,134 | 7/1975 | Scrivo | 433/29 |
| 3,958,114 | 5/1976 | Cadrino | 350/96.2 |
| 4,118,105 | 9/1978 | Voigt | 350/96.2 |

*Primary Examiner*—Robert Peshock
*Attorney, Agent, or Firm*—Blum, Kaplan, Friedman, Silberman & Beran

[57] ABSTRACT

An illuminator for a dental handpiece where the handpiece is of the type which has therein a light conductor that is small enough and light enough so that it can be mounted on and coupled directly to the handpiece. The light source in the illuminator is a quartz-halogen bulb. The illuminator housing provides for maintaining the quartz-halogen bulb at the necessary high temperature and in addition, provides for sufficient cooling and thermal insulation to protect the hand of the operator. The construction is such that a new bulb in its own housing can readily be substituted for the original on failure of the bulb.

30 Claims, 9 Drawing Figures

ILLUMINATOR FOR DENTAL HANDPIECE

REFERENCE TO RELATED APPLICATION

This is a continuation of application Ser. No. 129,511, filed Mar. 11, 1980, now abandoned, and is a continuation-in-part of our earlier application entitled Illuminator For Dental Handpiece, filed on Oct. 19, 1978, and having the Ser. No. 953,726 now abandoned. Said application is incorporated herein by reference as if fully presented.

BACKGROUND OF THE INVENTION

Illumination of the work area within the mouth has received a great deal of attention due to the importance of the problem, and a great variety of devices have been employed for this purpose, such devices including a reflector on the forehead of the dentist, overhead lights with special reflectors and special diffusors, and, more recently, fiber-optic bundles and light-conductors in the form of shaped plastic or glass rods. The fiber-optic bundle has received particular attention due to the fact that it can provide illumination which is concentrated at the head of the handpiece.

A preferred light-source for use in connection with fiber-optic bundles has been the projection-type halogen bulb inside a case which is cooled by an electric fan. The light emitted by this bulb is directed to one end of the flexible fiber bundle which runs the length of the dental air supply hose, the bundle being disposed either inside or outside the hose.

The preferred source of light pursuant to the present invention is a quartz-halogen bulb having a lens in the tip thereof to focus the light from a bulb on the end of the light conductor. For proper operation, the temperature of the light bulb must be high, a condition which results in the emission of considerable radiant heat. The quantity of heat emitted can be sufficiently great so that the enclosure could become unbearably hot to the hand of the operator if cooling means were not provided. Hutchinson U.S. Pat. No. 3,634,935 teaches the use of an incandescent lamp specifically excluding the use of a quartz-halogen lamp and copes with a lesser heat removal problem by passing water through a tubular coil in a chamber surrounding the light source. The use of a quartz-halogen lamp pursuant to the present invention requires a careful balance for effective cooling. If the cooling is too effective, the bulb will not operate at high efficiently, and if the cooling is inadequate, the enclosure can become uncomfortably hot. Another problem is that the quartz-halogen bulb may fail in use, in which case the dental procedure must be interrupted for replacement of the bulb. Where the bulb must be removed from a housing or from within a water-jacket as is the case with the Hutchinson device, the removal of the bulb can be a time-consuming as well as a delicate operation requiring skillful manipulation.

In our earlier application, we disclosed a construction which successfully copes with the problem of maintaining the bulb at high temperature while cooling the housing of the illuminator. However, it would be desirable to make it easier to replace the bulb rapidly and easily in the event of failure thereof. The present invention is designed to solve the problem of easy replacement of the bulb while maintaining the balance between cooling of the housing and the necessary high temperature of the bulb.

SUMMARY OF THE INVENTION

In accordance with the present invention, an illuminator for a dental handpiece is in the form of a cylindrical plug-in unit which mates with the handpiece and with sources of electric power, air and/or water. The unit includes a socket for a quartz-halogen light bulb in a cylindrical housing of a metal having high thermal conductivity, aluminum being preferred. The housing is covered by a retractable strain-relief shield of a metal of low thermal conductivity, stainless steel being preferred. The unit has lengthwise channels therethrough for transit of fluid such as water, drive air, chip air and exhaust. It also has insulated electrical contact pins for making electrical contact with a quartz-halogen bulb.

Excessive temperature rise of the illuminator is prevented by the flow of air therethrough. On the other hand, the socket is sized so that only the base of the bulb makes contact with the interior wall of the socket, clearance being provided between the bulb and the socket wall to minimize heat transmission therebetween. Further, the housing is so mounted to the shield that clearance is provided therebetween, thereby minimizing heat transfer from the housing to the shield which the operator must handle. In a first embodiment the bulb is directed distally and in a second embodiment is directed proximally.

A most important advantage of the present invention is that the mount of the unit in the shield is such that on retraction of the shield the unit can be readily unplugged from the handpiece and replaced as a unit on failure of a bulb. The structure is simple and inexpensive enough so that the unit can be regarded as disposable.

An object of the present invention is an illuminator for a dental handpiece where the illuminator is a plug-in unit including a high temperature, quartz-halogen bulb in which provision is made for providing the necessary high temperature for effective operation of the light bulb while protecting the hand of the operator and in which provision is made for rapid and easy replacement of the unit in the event of failure of the bulb.

Another object of the present invention is an illuminator for a dental handpiece wherein an effective balance of heat transfer and cooling is provided so that the quartz-halogen bulb in the illuminator can operate at maximum effectiveness without discomfort to the operator.

A further object of the present invention is an illuminator for a dental handpiece in which the plug-in unit which supports the quartz-halogen bulb therein can be discarded with the bulb in the event of failure thereof, and readily replaced with a fresh unit.

The invention accordingly comprises an article of manufacture possessing the features, properties, and the relation of elements which will be exemplified in the article hereinafter described, and the scope of the invention will be indicated in the claims.

BRIEF DESCRIPTION OF THE DRAWINGS

For a fuller understanding of the invention, reference is had to the following description taken in connection with the accompanying drawings in which.

DESCRIPTION OF THE PREFERRED EMBODIMENT

Figure 1:
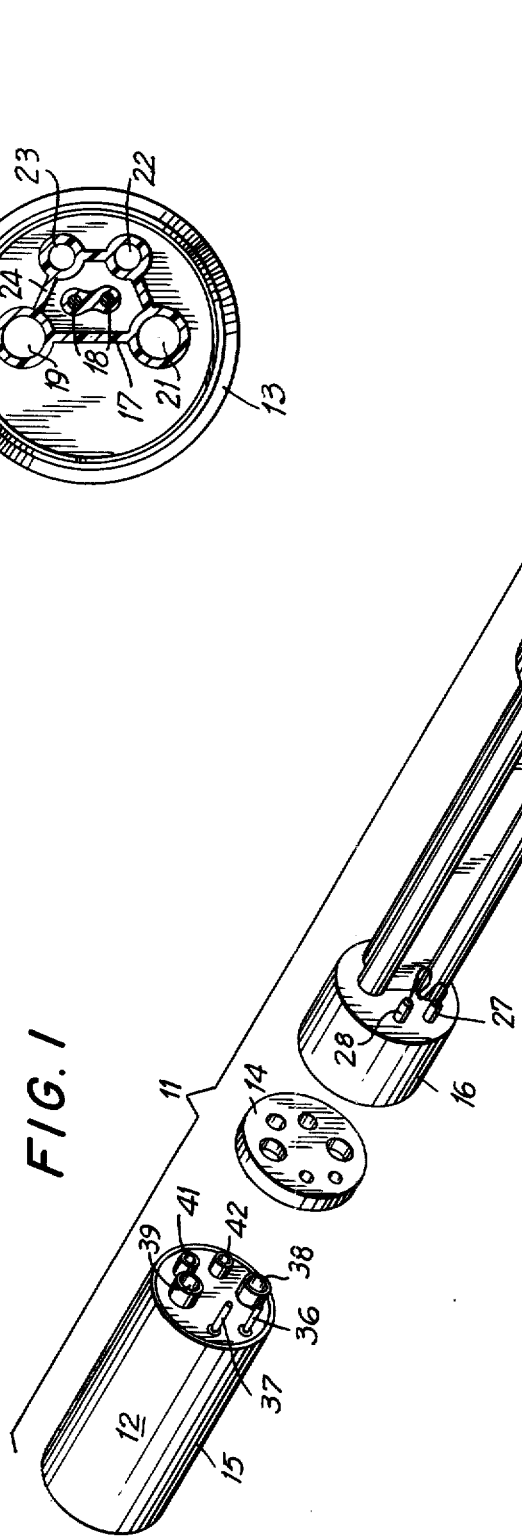
FIG. 1 is an exploded view in perspective of an illuminator in accordance with the present invention.
Figure 4:
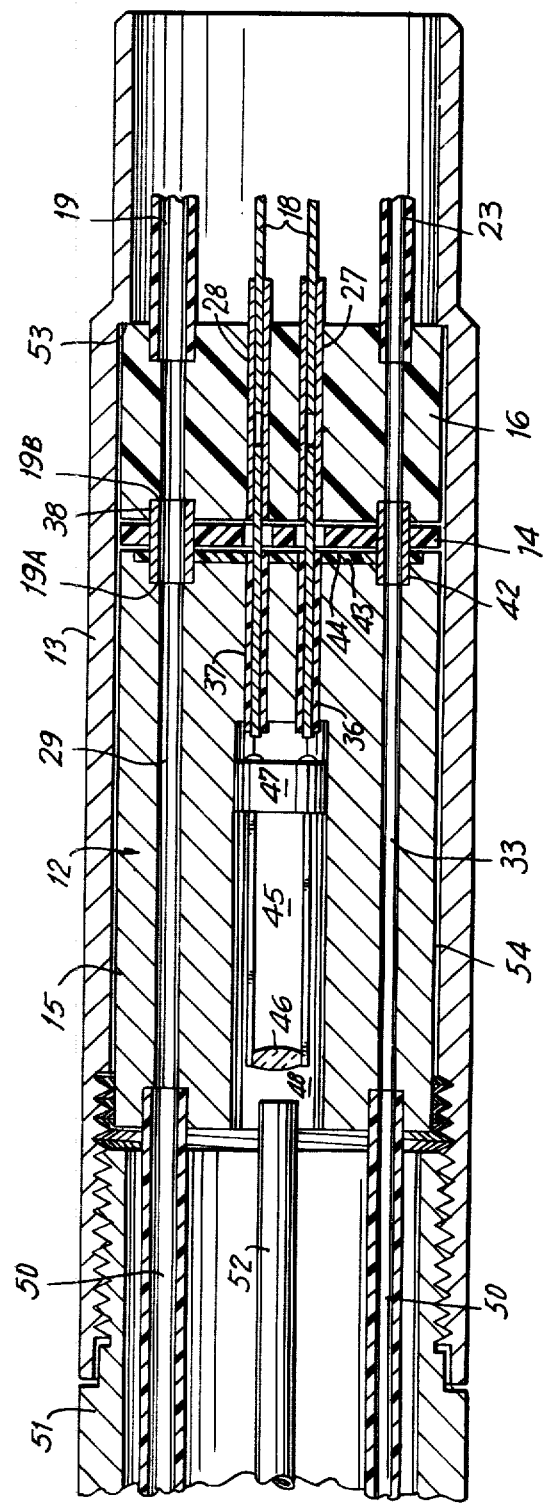
FIG. 4 is a sectional view taken along line 4—4 of FIG. 3.

An illuminator in accordance with the present invention is shown in exploded perspective view in FIG. 1, the illuminator being indicated generally by the reference numeral 11. Illuminator 11 comprises a plug-in unit 12 in a metal housing 15, a retractable strain-relief shield 13 which encloses the plug-in unit and connector 16 during the use thereof, and a gasket 14 which fits over the proximal end of the unit. The distal end of plug-in unit 12 fits the proximal end of a dental handpiece as shown in FIG. 4 and the proximal end of unit 14 fits the distal end of connector 16. Webbed handpiece tubing 17 is joined to connector 16 for conducting fluid therethrough and to said unit 12 and the dental handpiece connected thereto. The handpiece tubing also includes conductors 18 for powering a light bulb within the plug-in unit 12.

Figure 2:
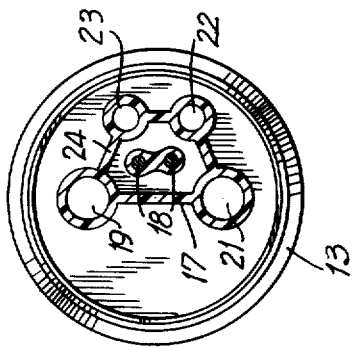
FIG. 2 is a sectional view taken along line 2—2 of FIG. 1.

The structure of a preferred webbed handpiece tubing 17 as shown in more detail in FIG. 2, said handpiece tubing preferably including two larger ducts 19 and 21 are two smaller ducts 22 and 23, thereby providing a total of four ducts which may be used, respectively, for feed of water, drive air and chip air to the handpiece and for return of exhaust air. Webbed tubing having three ducts is also satisfactory for many applications. Handpiece tubing 17 has a web 24 which forms an enclosure for containing therein the insulated conductors 18. Preferably, the insulated conductors are about 26 gauge and are of standard wire.

Figure 3:
FIG. 3 is an end view of plug-in unit 12 of FIG. 1.

The interior of connector 16 is made of a strong plastic having good insulating properties such as Delrin or Teflon which can withstand the temperature rise of the connector 16. It has seated therein two jacks 27 and 28 which are electrically connected as by soldering to the conductors 18, the wires 18 being taken out through a slit (not shown) in webbing 24. These jacks receive pins 36 and 37 of unit 12. Also, plug-in unit 12 has four channels therethrough (see FIGS. 3 and 4), these channels having the reference numerals 29, 31, 32 and plug-in unit 12. Preferably, webbing 24 is cut away from the individual ducts prior to seating the ducts in the channels in connector 16. Also, it is desirable that channels through unit 12 and connector 16 be provided with shoulders such as those at 19A and 19B (FIG. 4), against which the ends of corresponding metal alignment tubes 38, 39, 41 and 42 may seat for the purpose of increasing the tightness of the seal between the tubes and the channels through the unit and connector.

Gasket 14 fits over pins 36 and 37, large alignment tubes 38 and 39, and small alignment tubes 41 and 42, which protrude from unit 12. Gasket 14 provides resilience as well as insulation when the unit 12 is drawn firmly against connector 16 by strain relief shield 13 as will be detailed below. A thin wafer 43 of insulating material is also provided in a recess 44 (FIG. 4) in plug-in unit 12.

The internal construction of the illuminator is shown in enlarged scale in FIG. 4, which shows the quartz-halogen bulb 45 having a lens 46 at the distal end thereof, and supported at the proximal end thereof by base 47 in socket 48 in unit 12. Base 47 is electrically connected to contact pins 36 and 37 which are insulated from electrical contact with the housing 15, preferably of aluminum, these pins passing through wafer 43 and gasket 14 to make contact with jacks 27 and 28. Alignment tubes 38, 39, 41 and 42 are preferably of stainless steel and fit into channels 29, 31, 32 and 33 in connector 16. Preferably, these recesses are shaped for making contact against the ends of the tubing to insure a tight seal therebetween for transfer of fluid. Plug-in unit 12 is traversed by four channels, only two of which are shown in FIG. 4, these four channels corresponding to the four ducts in the handpiece tubing. The distal end of shield 13 may be threaded internally for mating with a correspondingly-threaded proximal end of a dental handpiece 51.

To assemble the illuminator and join same to a dental handpiece, gasket 14 is placed over the alignment tubes and pins of the plug-in unit, and the pins are inserted into the jacks of connector 16, the alignment tubes entering the corresponding channels in the connector. The dental handpiece 51 is then mated with the plug-in unit so that light-conductor 52 of the handpiece enters socket 48 and the fluid-transport tubes 50 thereof enter the corresponding channels in unit 12. Retractable shield 13 is then brought up to the proximal end of dental handpiece 51 and threaded onto same. As the threading proceeds, shoulder 53 of shield 13 makes contact with the proximal end of connector 16, forcing same toward the dental handpiece and bringing all the elements of the illuminator into tight, sealing contact. In the event of failure of the light bulb 45, the procedure is reversed, freeing plug-in unit 12 from shield 13, the gasket 14, and connector 16, and the unit is simply replaced with a fresh unit.

An important feature of the present invention is the clearance 54 between shield 13 and unit 12, this clearance serving as an impedance to the transfer of heat from unit 12 to shield 13 which must be handled by the operator. It is a combination of this clearance which is preferably about 0.020 inches with the cooling provided by the fluids traversing the channels of the unit which minimizes the heat transfer to the exterior of the stainless steel shield 13 so that it can readily be handled by the operator without discomfort. Similarly, it is the clearance between the quartz-halogen bulb 45 and the wall of socket 48 which permits the bulb to stay hot enough for maximum effectiveness.

Figure 5:
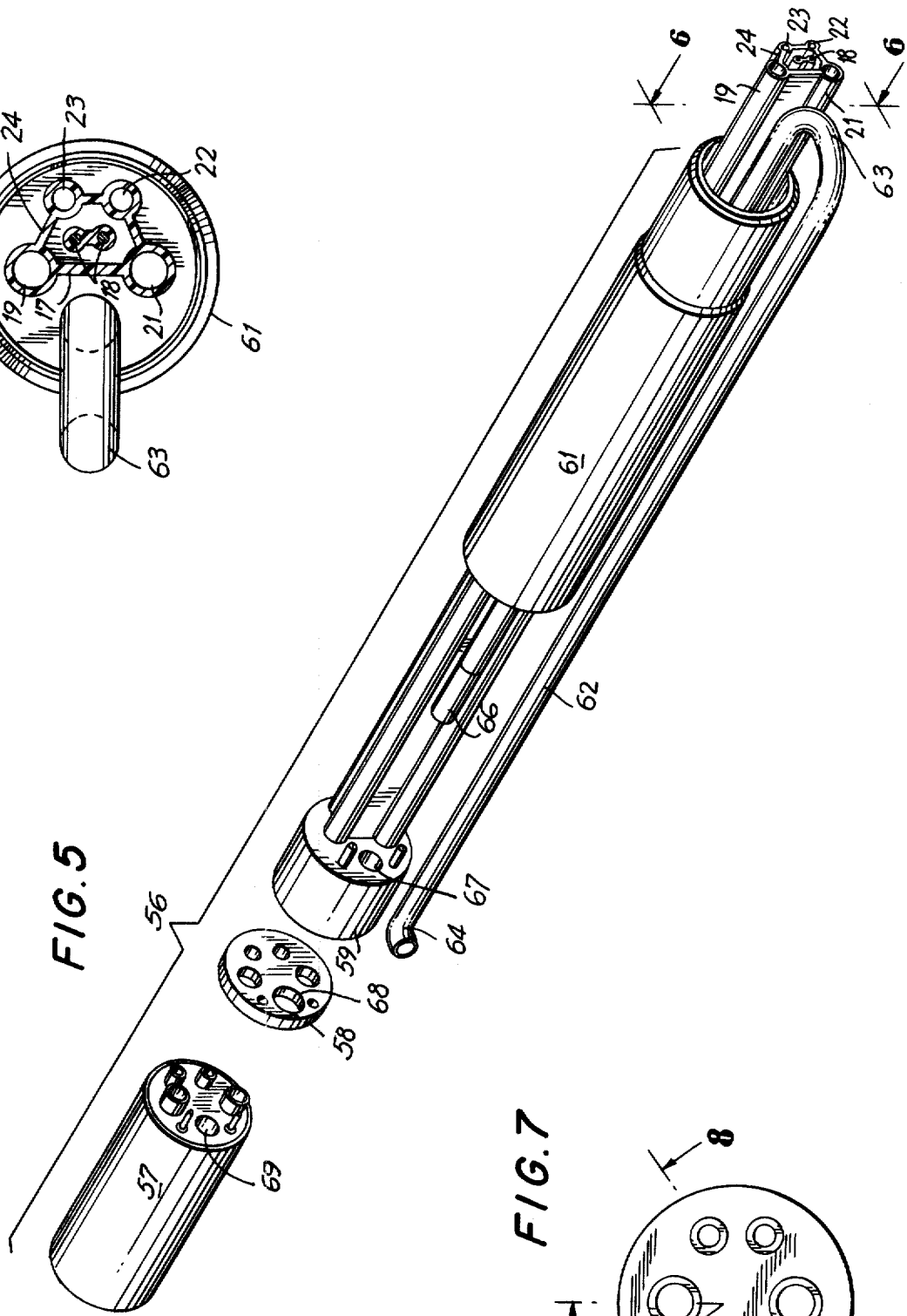
FIG. 5 is an exploded view in perspective of another embodiment of the invention.

The embodiment of FIGS. 1-4 is suitable for use with a dental handpiece which includes means for conveying light from the bulb of the plug-in unit to the work region of the handpiece. The means for conveying light may be a fiber-optic bundle or a suitably shaped transparent rod having a high index of refraction. Where an illuminator in accordance with the present invention is to be coupled to a dental handpiece which lacks a light conveyor, the embodiment of the invention shown in FIGS. 5-8 may be used. Referring first to FIG. 5, an illuminator indicated generally by the reference numeral 56 includes a plug-in unit 57 and gasket 58, a connector 59 and a strain-relief shield 61. In addition, the illuminator includes light-pipe 62 of a material having a high degree of transparency and a high index of refraction. It is preferable to use glass although methyl methacrylate may also be used. The pipe has a 180° bend at region 63 and is preferably curved at region 64 to direct light toward a work area. Stem end 66, during assembly of the illuminator, passes through channels 67 and 68, respectively, in connector 59 and gasket 58 and into opening 69 in plug-in unit 57. So far as gasket 58 and connector 59 are concerned, these elements of the illuminator are identical with elements 14 and 16 of the embodiment of FIGS. 1-4, except for channels 67 and 68.

Figure 6:
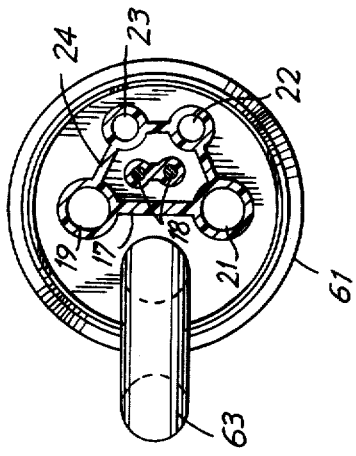
FIG. 6 is a sectional view taken along line 6—6 of FIG. 5.

FIG. 6 is a sectional view taken along line 6—6 of FIG. 5 and clearly shows that the only difference between connector 59 and connector 16 is the presence of channel 67 in connector 59. Like features in the two Figures have the same reference numerals.

Figure 7:
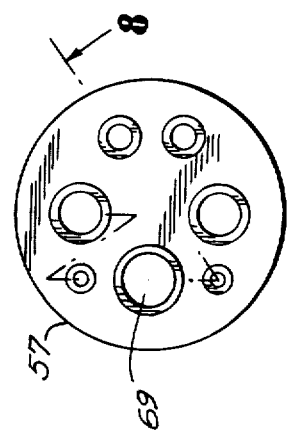
FIG. 7 is an end view of the embodiment of FIG. 5.
Figure 8:
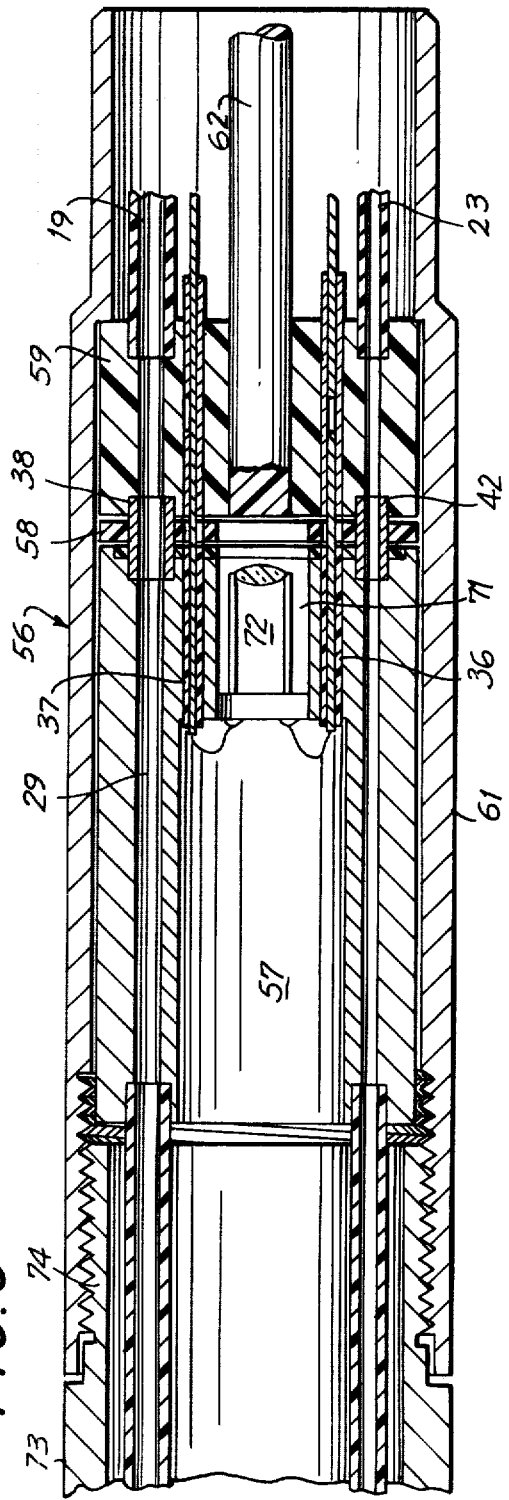
FIG. 8 is a sectional view taken along line 8—8 of FIG. 6.

As can be seen from FIG. 4, socket 48 and bulb 45 are oriented for directing light distally, whereas light-pipe 66 (FIG. 5) enters plug-in unit 57 from the proximal end. Accordingly, it is necessary that plug-in unit 57 be constructed so that light from the bulb therein will be projected proximally. FIG. 8 which is a section taken along the broken line 8—8 of FIG. 7 illustrates the construction of plug-in unit 57. Said plug-in unit includes a socket 71 in which a bulb 72 is seated, the socket and bulb being oriented for directing light to the proximal end of plug-in unit 57. The light from bulb 72 enters light-pipe 62 to be conveyed to the work area of dental handpiece 73. Dental handpiece 73 is shown as being held firmly against plug-in unit 57 by means of internal threads 74 mating with strain-relief shield 61. As is evident, either embodiment of the illuminator of the present invention can be held to a dental handpiece by other means such as an appropriate collar.

Figure 9:
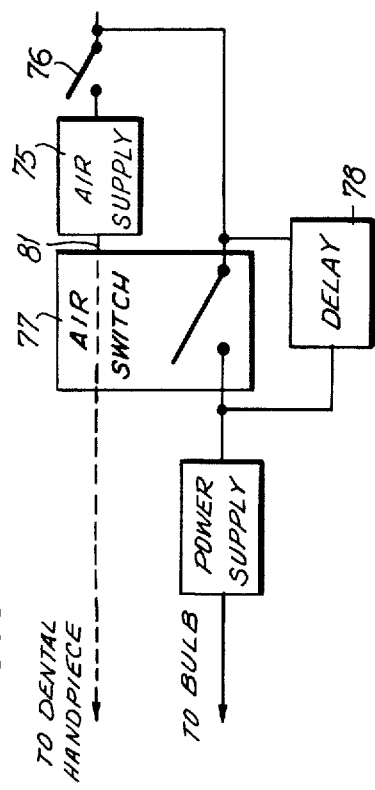
FIG. 9 shows diagrammatically air and electric power connections for said illuminator.

In the operation of a dental handpiece, it is desirable to be able to view the field of work after cutting the supply of drive air. On the other hand, it is necessary to ensure that the illuminator be cooled during operation and that the illuminator be shut off when operation of the dental handpiece is interrupted. To achieve these purposes, the power supply (FIG. 9) is so constructed that closing switch 76 activates only the air supply 75 to the dental handpiece. Flow of air through air switch 77 on its way to the handpiece closes the air switch so that electric power flows to the bulb 45 in the plug-in unit. However, when switch 76 is opened, switch 77 is also opened and the air supply is immediately terminated but delay unit 78 comes into play and provides power to the bulb for a selected short period thereafter, a few seconds being generally sufficient to permit the operator to view the work region after cutting off the air supply. The delay period is generally set for a short enough period so that the build-up of heat in the plug-in unit, cooling air having been cut off, is not sufficient to cause any difficulty to the operator. Air switch 77 can be positioned at any point in supply tubing 81 leading from air power supply 75 to connector 16 or 59.

As will be evident, the illuminators of the present invention preserve a delicate balance between maintaining the high temperature necessary for effective operation of the quartz-halogen light bulb and preventing discomfort to the operator by minimization of heat transfer to the exterior of the device. Simultaneously, they provide for easy and inexpensive replacement of the bulb as part of a plug-in unit when a bulb fails.

It will thus be seen that the objects set forth above among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. Illuminator for a dental handpiece, said illuminator, when in use, generating a quantity of heat such that provision for preventing excessive temperature rise at the exterior thereof must be made while maintaining a high enough temperature in the interior thereof for satisfactory operation of same, comprising: replaceable plug-in unit means of generally cylindrical shape with a proximal and a distal end, said unit means including a cylindrical housing of a metal of high thermal conductivity, said unit means having an axially directed socket in one end thereof, said unit means including a quartz-halogen bulb seated in said socket with clearance between the wall of said socket and said bulb, said socket being open at said one end for transmission of light in a generally axial direction toward said handpiece, said unit means having at least one channel leading therethrough from said proximal to said distal end for transit of fluid therethrough, alignment tube means seated in the proximal end of each said channel, and pins protruding from said proximal end of said unit means for seating in jacks for bringing current to said pins;

connector means of an insulating material, said connector means having a proximal and a distal end, and including electrical jacks for receiving said pins for making contact therewith, said connector means having at least one channel therethrough for receiving each of said alignment tubes in the distal end thereof for transit of fluid between said connector means and said unit means and for receiving in the proximal end thereof supply tubing whereby fluid may be transferred between said supply tubing and said dental handpiece through said connector means and said unit means; and generally cylindrical, hollow shield means arranged and constructed for holding said connector means and for holding said unit means with clearance, said shield means being of a material of low thermal conductivity and having a proximal end and a distal end, said shield means having an internal shoulder for bearing against the proximal end of said connector means, and said shield means including attachment means for receiving a dental handpiece and drawing the proximal end thereof into tight contact with the distal end of said unit means.

2. Illuminator as defined in claim 1, wherein said end at which said socket is open is the distal end of said unit means, whereby said unit means is suitable for joining with a handpiece having a light conductor at the proximal end thereof.

3. Illuminator as defined in claim 1, wherein said end at which said socket is open is the proximal end of said unit means, and said connector means includes light conductor means constructed and arranged for receiving light from said quartz-halogen bulb and conveying said light to the work region of a dental handpiece.

4. Illuminator as defined in claim 1, wherein said shield means is of stainless steel.

5. Illuminator as defined in claim 1, further comprising gasket means disposable between the proximal end of said unit means and the distal end of said connector means.

6. Illuminator as defined in claim 1, wherein said unit means has a recess in the proximal end thereof and further comprising insulating sheet means in said recess, said sheet means having apertures therein for transit therethrough of said alignment tube means and said contact pins.

7. Illuminator as defined in claim 1, wherein said housing is of aluminum.

8. Illuminator as defined in claim 1, wherein the number of channels in each of said unit means and said connector means is four and the number of alignment tube means is four, one of said tube means being seated in each of said channels, thereby providing for transit of drive air to said handpiece, chip air, cooling water and exhaust.

9. Illuminator as defined in claim 1, further comprising webbed handpiece tubing means connected with the proximal end of said connector means for transfer of fluid therebetween, said tubing means including electrical conductors electrically-connected with said jacks.

10. Illuminator as defined in claim 1, further comprising electrically powered air supply means for providing air to said dental handpiece, electric power supply means for activating said bulb, switch means for activating said air-supply means, air supply tubing means for transfer of air from said air supply means to said dental handpiece, air switch means in said air supply tubing means for connecting said electric power supply means to said bulb when air flows through said tubing means and delay means connected with said air switch means for providing that on opening said switch means power to said bulb will continue for a short interval after inactivating said air-supply means, thereby permitting an operator to inspect his work after cutting off the supply of air to said handpiece and ensuring that power to the bulb will shortly be terminated after opening said switch means.

11. Plug-in unit means for proving illumination to a dental handpiece, said unit means having a housing of a metal of high thermal conductivity and being generally cylindrical in shape with a distal end and a proximal end and having a socket in one end thereof, said unit means including a quartz-halogen bulb seated in said socket with clearance between said bulb and the wall of said socket, said unit means having at least one channel therethrough from the proximal end to the distal end thereof for transit of fluid, said unit means including pins electrically connected with said bulb and protruding from said proximal end, the proximal end of said unit means being shaped for connecting replaceably with electrical supply means, with cooling fluid supply means and with air supply means, and the distal end of said unit means being shaped for connecting replaceably with a dental handpiece.

12. Plug-in unit means as defined in claim 11, wherein said housing is of aluminum.

13. Plug-in unit means as defined in claim 11, wherein the number of channels in said unit means is four, alignment tube means being seated in the proximal end of each of said channels.

14. Plug-in unit means as defined in claim 11, wherein said unit means has a recess in the proximal end thereof and includes a sheet of insulator material in said recess.

15. Plug-in unit means as defined in claim 11, wherein said unit means includes alignment tube means seated in the proximate end of each of said channels.

16. Plug-in unit means as defined in claim 1, wherein said socket is in the distal end of said unit means and is arranged and constructed for receiving the proximal end of a light-conductor in said handpiece.

17. Plug-in unit means as defined in claim 1, wherein said socket is in the proximal end of said unit means and is arranged and constructed for receiving an end of a light conductor.

18. Illuminator for a dental handpiece, said illuminator, when in use, generating a quantity of heat such that provision for preventing excessive temperature rise at the exterior thereof must be made while maintaining a high enough temperature in the interior thereof for satisfactory operation of same, comprising plug-in unit means with a proximal and a distal end, said unit means including a housing of a metal of high thermal conductivity, said unit means having an axially directed socket in one end thereof, said unit means including a quartz-halogen bulb seated in said socket with clearance between the wall of said socket and said bulb, said socket being open at said one end for transmission of light in a generally axial direction toward said handpiece, said unit means having at least one channel leading therethrough from said proximal to said distal end for transit of driving air therethrough;

connector means of an insulating material, said connector means having a proximal and a distal end and having at least one channel therethrough for registry with said unit means channel for transit of driving air between said connector means and said unit means and for receiving in the proximal end thereof supply tubing whereby fluid may be transferred between said supply tubing and said dental handpiece through said connector means and said unit means; and hollow shield means arranged and constructed for holding said connector means and said unit means with clearance, said shield means being of a material of low thermal conductivity and including attachment means for receiving a dental handpiece and drawing the proximal end thereof into tight contact with the distal end of said unit means.

19. An illuminator for a dental handpiece, said illuminator, when in use, generating a quantity of heat such that provision for preventing excessive temperature rise at the exterior therof must be made while maintaining a high enough temperature in the interior thereof for satisfactory operation of same, comprising a replaceable housing of a metal of high thermal conductivity with a distal end and a proximal end and having a socket in one end thereof, a quartz-halogen bulb seated in said socket with clearance between said bulb and the wall of said socket, said housing having at least one channel therethrough from the proximal end to the distal end thereof for transit of driving air therethrough, means for replaceably connecting said bulb to a power source external of said housing, and hollow shield means for holding said housing with clearance and for holding said housing to said dental handpiece, said shield means being of a material of low thermal conductivity to minimize heat transfer from the housing.

20. An illuminator as defined in claim 19, further comprising first switch means for activating said driving air, and second switch means activated by said driving air and in circuit with said bulb power source for activating said bulb.

21. An illuminator as defined in claim 20, further comprising delay means connected with said second switch means for providing that on opening of said second switch means power to said bulb will continue for a short interval after inactivating said first switch means.

22. An illuminator for a dental handpiece disposed immediately proximal to the hand-piece for providing high intensity light for illumination of a work area, comprising:
   a high intensity halogen bulb which generates heat during use located in said illuminator;
   channel means including at least one channel therethrough formed of a material of high thermal conductivity adjacent to the bulb for transit of fluid to the distal end of said handpiece with clearance between said bulb and said channel means and for removal of heat generated by the bulb;
   hollow shield means formed from a material having a low thermal conductivity surrounding said bulb and channel means and including means for coupling to the handpiece, said shield means spaced apart from said bulb and channel means.

23. The illuminator of claim 22, wherein said at least one channel is for supplying driving air to the handpiece.

24. The illuminator of claim 23, wherein said channel means is a housing of a material of high thermal conductivity formed with a socket for receiving said bulb and at least one channel formed through said housing, said bulb seated in said housing and spaced apart therefrom.

25. The illuminator of claim 24, wherein said socket for receiving said bulb is formed in the proximal end of said housing.

26. The illuminator of claim 24, wherein said socket for receiving said bulb is formed in the distal end of said housing.

27. The illuminator of claim 24, wherein said bulb is encased within said housing and said housing is replaceably mounted in said illuminator.

28. The illuminator of claims 25, 26 or 27, further comprising first switch means for activating said driving air, and second switch means activated by said driving air and in circuit with said bulb power source for activating said bulb.

29. The illuminator of claim 28, further comprising delay means connected with said second switch means for providing that an opening of said second switch means power to said bulb will continue for a short interval after inactivating said first switch means.

30. An illuminator for a dental handpiece disposed immediately proximal the handpiece for providing high intensity light for illumination of a work area, comprising:
   a substantially cylindrical housing of a material of high thermal conductivity formed with a socket for receiving a bulb;
   a high intensity halogen bulb which generates that during use seated in said pocket;
   at least one channel formed through the housing adjacent to the bulb for transit of fluid to the distal end of said handpiece with clearance between said bulb and said housing and for removal of heat generated by the bulb; and
   hollow shield means formed from a material having a low thermal conductivity surrounding said housing and including means for coupling to the handpiece, said shield means spaced apart from said housing.

* * * * *